US00PP18850P2

(12) United States Plant Patent
Carruth

(10) Patent No.: US PP18,850 P2
(45) Date of Patent: May 27, 2008

(54) FLORIBUNDA ROSE PLANT NAMED 'WEKSMOPUR'

(50) Latin Name: *Rosa hybrida*
Varietal Denomination: WEKsmopur

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 43 days.

(21) Appl. No.: 11/602,722

(22) Filed: Nov. 21, 2006

(51) Int. Cl.
*A01H 5/00* (2006.01)

(52) U.S. Cl. ..... Plt./141

(58) Field of Classification Search ..... Plt./141
See application file for complete search history.

*Primary Examiner*—Annette H Para
(74) *Attorney, Agent, or Firm*—McKee, Voorhees & Sease, P.L.C.

(57) ABSTRACT

A new variety of Floribunda rose suitable for garden decoration, having flowers of deep plum coloration.

1 Drawing Sheet

Classification: The present invention relates to a new *Rosa hybrida* plant.

Variety denomination: The new plant has the varietal denomination 'WEKsmopur'.

BACKGROUND OF THE INVENTION

This invention relates to a new and distinct variety of Floribunda Rose. It has an undisseminated seedling of Applicant's creation as its seed parent with the following genetic origin (Sweet Chariot×Blue Nile)×Stephen's Big Purple and has an undisseminated seedling of Applicant's creation as its pollen parent with the following genetic origin (International Herald Tribune×*Rosa soulieana* derivative)×(Sweet Chariot×Blue Nile).

SUMMARY OF THE INVENTION

Among the features which distinguish the new variety from other presently available and commercial rose cultivars known to the inventor are the following combination of characteristics: its strong citrus-like to moderately spicy fragrance, its hairy flower receptacle, its mucronate petal apices, its nearly horizontal zone of lighter coloration forming a broad 'V' shaped at the petal base, its very low-thorned new shoots and branches and its unusual deep plum flower coloration. The plant has a rounded and compact growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKsmopur' may be asexually propagated by cuttings, budding and grafting. The budding and grafting successfully occurred on the plant/rootstock *Rosa hybrida* cv. 'Dr. Huey'.

COMPARISON WITH PARENTS

The new rose may be distinguished from its seed parent, an undisseminated seedling of Applicant's creation by the following combination of characteristics: whereas 'WEKsmopur' bears medium sized flowers (about 8.0 to about 10.2 cm. in diameter) of deep plum coloration, the undisseminated seedling bears significantly larger flowers (about 9.7 to 13.9 cm. in diameter) of a lighter purple-pink coloration. The seed parent bears matte foliage, whereas 'WEKsmopur' bears glossy foliage.

The new variety may be distinguished from its pollen parent, an undisseminated seedling of Applicant's creation by the following combination of characteristics: whereas 'WEKsmopur' bears very double flowers (about 25 to 48 petals) of deep plum coloration, the undisseminated seedling bears semi-double flowers of lavender coloration with significantly lesser petalage (about 14 to 23 petals). The new variety is classified as a floribunda rose with a rounded and compact low height mature growing habit (about 66 to about 80 cm. in height), whereas the pollen parent is classified as a shrub rose with a moderately spreading significantly taller mature growing habit.

COMPARISON WITH THE CLOSEST COMMERCIALLY AVAILABLE CULTIVAR

The new variety may be distinguished from its closest commercially available cultivar, 'WEKfabpur' U.S. Plant Pat. No. 16,623 by the following combination of characteristics: whereas 'WEKsmopur' bears very double flowers (about 25 to 48 petals) of deep plum coloration, 'WEKfabpur' bears semi-double flowers of velvety black purple coloration with a white eye and with significantly lesser petalage (about 18 to 24 petals). The new variety bears medium size flowers (about 8.0 to about 10.2 cm. in diameter), whereas the closest commercially available cultivar bears significantly smaller flowers (about 5.3 to about 7.4 cm. in diameter).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of November. Phenotypic expression may vary with environmental, cultural and climatic conditions, as well as differences in conditions of light and soil.

Botanical designation: The new variety botanical designation is *Rosa hybrida* 'WEKsmopur'.

FLOWER

The new variety sometimes bears its flowers singly, usually in clusters of two to five or more per stem. Flowers may be borne in regular rounded clusters on strong somewhat short to medium length stems (about 18 to about 50 cm.). Outdoors, the plant blooms abundantly and nearly continuously during the growing season. The flowers have a strong citrus-like to moderately spicy fragrance.

BUD

The peduncle is about 2.9 to about 6.6 cm. in length, of average caliper (about 0.2 to about 0.3 cm. in diameter), and usually erect. It is moderately smooth, with some stipitate glands and many hairs. Peduncle color is between 146C and 148B often moderately suffused, especially on the side exposed to the sun, with between 187B and 183B.

Before the calyx breaks, the bud is about 0.9 to about 1.6 cm. in diameter at the widest point, about 1.1 to about 1.5 cm. in length, and moderately ovoid to somewhat pointed in shape. The surface of the bud bears few foliaceous appendages and some stipitate glands and hairs, usually with slender entire foliaceous parts extending beyond the tip of the bud about ¼ or more of its length. Bud color is between 146B and 146C sometimes lightly suffused, especially on the side exposed to the sun, with between 187C and 183C.

The sepals are about 2.0 to about 4.5 cm. in length and about 0.6 to about 1.0 cm. in width at the widest point. The outer surface color of the sepal is between 146B and 146C sometimes lightly suffused, especially on the side exposed to the sun, with between 187C and 183C. The inner surface color of the sepal is between 137A and 138B. After the sepals open, the inner surface color is sometimes lightly suffused, especially on the area exposed to the sun, with between 187C and 183B. The inner surface is covered with fine wooly tomentum; sepal margins are lined with many stipitate glands and hairs.

The receptacle of the flower is of moderately short to medium length (about 0.5 to about 0.8 cm.) and average in caliper (about 0.6 to about 0.8 cm. in diameter). The receptacle is moderately rounded to somewhat urn-shaped in form. Its surface is very smooth with some hairs and with thick fleshy walls. The receptacle color is between 144A and 147B often moderately suffused, especially on the side exposed to the sun, with between 187B and 187A.

As the petals open (after the calyx breaks), the bud is about 1.2 to about 2.6 cm. in diameter at the widest point, about 1.5 to about 3.0 cm. in length, and moderately ovoid to somewhat globular in form. The color of the under surfaces of the newly opened petals is between 59B and 60C gradually suffusing toward the petals edge with darker than between 187A and 79A. At the point where the petal attaches, there is a moderately large zone of between 1C and 154C. The color of the upper surfaces of the newly opened petals is between 59A and 71A gradually suffusing toward the petals edge with darker than between 187A and 79A. At the point where the petal attaches, there is a moderately large zone of between 2B and 3B.

BLOOM

When fully open, the bloom ranges from about 8.0 to about 10.2 cm. in diameter. Petalage is very double with about 25 to 48 petals and about 11 to 19 petaloids irregularly arranged. When partially open, the bloom form is globular to somewhat high centered, and the petals are moderately tightly spiraled to somewhat cupped with petal edges slightly reflexed outward. When fully open, the bloom form is cupped, and the petals are loosely cupped to moderately undulated with petal edges somewhat reflexed outward.

PETALS

The substance of the petals is moderately heavy and of somewhat thick thickness, with upper surfaces moderately velvety to satiny and under surfaces slightly shiny to matte. The petals are about 2.7 to about 4.9 cm. in length and about 2.3 to about 4.9 cm. in width at the widest point. Petal margins are entire.

The outer petals are nearly rounded to somewhat obovate in shape with usually mucronate and sometimes rounded apices.

The inner petals are broadly obovate in shape with usually mucronate and sometimes rounded apices.

Petaloids are about 1.2 to about 3.3 cm. in length and about 0.6 to about 3.0 cm. in width at the widest point. Petaloids are irregularly shaped somewhat oblanceolate to subulate with rounded apices.

NEWLY OPENED FLOWER

The under surface color of the outer petals is between 72A and darker than 71A. At the point where the petal attaches, there is a moderately large zone of between 2D and 4D. The upper surface color of the outer petals is between 74B and 64A lightly suffused with between 79B and 71A. At the point where the petal attaches, there is a moderately large zone of between 3D and 4C. On either side of this attachment point, extending to the edge of the petal, there is a moderately wide, nearly horizontal zone of lighter coloration forming a broad 'V'. The coloration of this chevron is between 70B and 74C.

The under surface color of the intermediate petals is between 72A and 70A. The upper surface color of the intermediate petals is between 74B and 64A moderately suffused with between 79A and darker than 71A.

The under surface color of the inner petals is between 72A and 70A. The upper surface color of the inner petals is between 74B and 64A heavily suffused with between 79A and darker than 71A.

The under and upper surface color of the petaloids are similar in coloration to the upper and under surfaces of the inner petals.

The general tonality of the newly opened flower is between 74B and 64A suffused with between 79A and darker than 71A.

THREE-DAY-OLD FLOWER

The under surface color of the outer petals is between 80B and 78B. At the point where the petal attaches, there is a moderately large zone of between 155A and 4D. The upper surface color of the outer petals is between 80B and 74B moderately suffused with between 79B and 79A. At the point where the petal attaches, there is a moderately large zone of between 4D and 2D. On either side of this attachment point, extending to the edge of the petal, there is a moderately wide, nearly horizontal zone of lighter coloration forming a broad 'V'. The coloration of this chevron is near 155C.

The under surface color of the intermediate and inner petals is between 80C and 70A. The upper surface color of the intermediate and inner petals is between 78B and 74B heavily suffused with between darker than 79B and 79A.

The under and upper surface color of the petaloids are similar in coloration to the upper and under surfaces of the intermediate and inner petals.

The general tonality of the three-day-old flower is between 80B and 74B heavily suffused with between darker than 79B and 79A.

On the spent bloom, the petals usually drop off cleanly.

In November in Upland, Calif., blooms on the bush growing outdoors generally last about four to five days. Cut roses from plants grown outdoors and kept at normal indoor living temperatures generally last about four to five days.

MALE REPRODUCTIVE ORGANS

Stamens are few in number (average about 50) and are arranged regularly about the pistils; some are mixed with petaloids. The filaments are of medium length (about 0.5 to about 0.9 cm.) most with anthers. Filaments are between 4C and 2D in color sometimes lightly suffused with between 53B and 53C. The anthers are somewhat small for the class and all open approximately at the same time. Anther color when immature is near 17A on the external part and near 16D on the internal part. Anther color at maturity is between 163C and 161B on the external part and near 200B on the internal part. Pollen is somewhat abundant and between 18B and 19C in color.

FEMALE REPRODUCTIVE ORGANS

Pistils vary in number (average about 45). The styles are moderately even, somewhat long in length (about 0.8 to about 1.1 cm.), thin to average in caliper and loosely bunched to somewhat separated. Stigma color is between 16C and 15D. Style color is between 1C and 1D often moderately suffused with between 53B and 53C. Ovaries are usually all enclosed in the calyx.

Hips are of average length (about 1.0 to about 1.4 cm.), very rounded in form, and between 28B and 30B in color when ripe. The hip surface is very smooth with thick fleshy walls. The sepals are moderately permanent and usually straight in shape.

The seeds are irregularly rounded, smooth in texture, approximately 7 to about 11 per hip, about 0.5 to about 0.7 cm. in diameter at the widest point and near 161B in color.

FOLIAGE

The compound leaves are usually comprised of three to five leaflets and are borne abundantly. The five-leaflet leaves are about 8.7 to about 13.3 cm. in length and about 6.9 to about 10.5 cm. in width at the widest point, moderately leathery in texture, and glossy in finish. The terminal leaflets are about 4.4 to about 6.6 cm. in length and about 2.6 to about 4.5 cm. in width at the widest point, shaped moderately oval to somewhat ovate with acute to somewhat acuminate apices and rounded to moderately acute bases. Their margins are usually simply serrate.

The upper surface color of the mature leaf is between 139A and 147A. The under surface color of the mature leaf is between 147B and 148B. The upper surface color of the young leaf is between 139B and 146D, often heavily suffused with between 187A and 183B. The under surface color of the young leaf is between 137D and 146D, often heavily suffused with between 187B and 183A.

The rachis is moderately light in caliper and very smooth. The upper side is shallowly grooved with some hairs and few stipitate glands on the edges of the grooves. The under side of the rachis is very smooth with some hairs and very few stipitate glands. The rachis color is near 146D on the under side and near 138A on the upper side, often heavily suffused especially on the young leaf with between 187B and 183B.

The stipules are about 1.0 to about 1.6 cm. in length and medium in width (about 0.6 to about 0.8 cm.) with very long straight points that usually turn out at an angle of more than 45 degrees and sometimes recurve toward the stem. The stipules color is between 137B and 146B.

The petiole is moderately light in caliper and very smooth. The upper side is shallowly grooved with some hairs and few stipitate glands on the edges of the grooves. The under side of the petiole is very smooth with some hairs and very few stipitate glands. The petiole is about 0.4 to about 1.2 cm. in length and about 0.1 to about 0.15 cm. in diameter at the widest point. The petiole color is near 146D on the under side and near 138A on the upper side, often heavily suffused especially on the young leaf with between 187B and 183B.

The plant displays an average degree of resistance to powdery mildew and rust as compared to other commercial varieties grown under comparable conditions in Upland, Calif. The plant's winter hardiness and drought/heat tolerance are yet to be determined.

GROWTH

The plant has a rounded and compact low height mature growing habit (about 66 to about 80 cm. in height and about 54 to about 72 cm. spread at the widest point), with full branching. It displays moderately vigorous growth and the canes are of somewhat light caliper for the class.

The color of the major stems is between 147B and 146A. They bear few large prickles that are about 0.5 to about 0.7 cm. in length. The large prickles are almost straight to angled slightly downward with a medium length somewhat narrow oval base; prickle color is between 166B and 166C. The major stem bears few small prickles of similar shape and coloration.

The color of the branches is between 146A and 148B. They usually bear no large prickles but sometimes bear very few large prickles which are of similar size and shape to the large prickles on the major stems; prickle color is between 164B and 164A. The branches usually bear no small prickles but sometimes bear very few small prickles of similar shape and coloration.

The color of the new shoots is between 145A and 146C often heavily suffused with between 187B and 183A. They usually bear no large prickles but sometimes bear very few large prickles which are of similar size and shape to the large prickles on the major stems; prickle color is near 151A usually moderately suffused with between 187B and 187C. The shoots usually bear no small prickles but sometimes bear very few small prickles of similar shape and coloration.

I claim:

1. A new and distinct Floribunda rose plant of the variety substantially as described and illustrated herein.

* * * * *

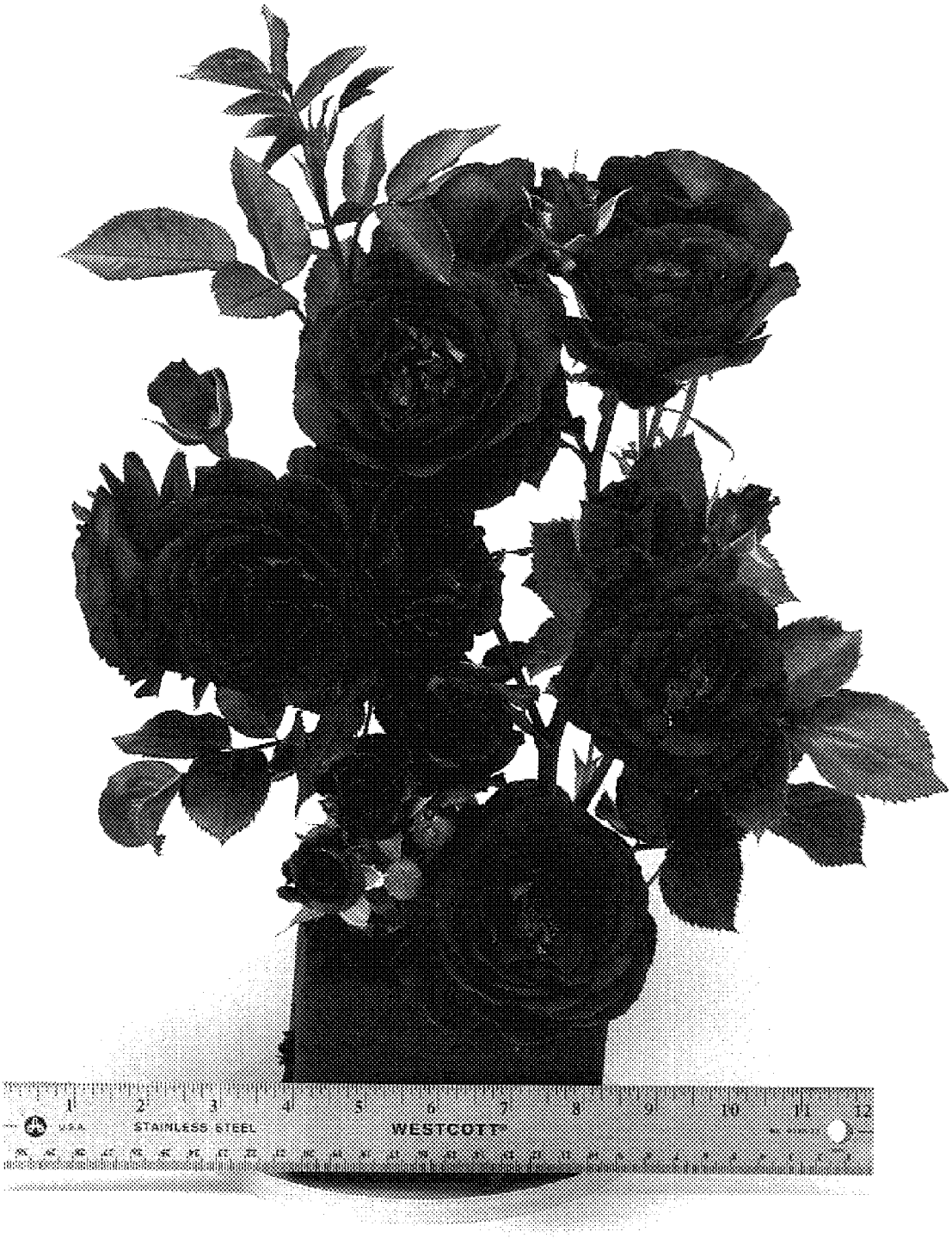
STAINLESS STEEL
WESTCOTT